(12) United States Patent
Lee et al.

(10) Patent No.: US 10,007,984 B2
(45) Date of Patent: Jun. 26, 2018

(54) METHOD FOR QUANTIFYING MEDICAL IMAGE

(71) Applicant: The Asan Foundation, Seoul (KR)

(72) Inventors: Min Ho Lee, Seoul (KR); Nam Kug Kim, Seoul (KR); Joon Beom Seo, Seoul (KR)

(73) Assignee: The Asan Foundation, Seoul (KR)

( * ) Notice: Subject to any disclaimer, the term of this patent is extended or adjusted under 35 U.S.C. 154(b) by 0 days. days.

(21) Appl. No.: 15/049,666

(22) Filed: Feb. 22, 2016

(65) Prior Publication Data

US 2016/0171689 A1    Jun. 16, 2016

Related U.S. Application Data

(63) Continuation of application No. PCT/KR2014/004974, filed on Jun. 4, 2014.

(30) Foreign Application Priority Data

Aug. 20, 2013    (KR) .................. 10-2013-0098549

(51) Int. Cl.
| | |
|---|---|
| *G06K 9/00* | (2006.01) |
| *G06T 7/00* | (2017.01) |
| *A61B 6/00* | (2006.01) |
| *A61B 6/03* | (2006.01) |
| *G06K 9/40* | (2006.01) |
| *G06K 9/46* | (2006.01) |

(Continued)

(52) U.S. Cl.
CPC ............ *G06T 7/0012* (2013.01); *A61B 6/032* (2013.01); *A61B 6/50* (2013.01); *A61B 6/5211* (2013.01); *A61B 6/5258* (2013.01); *G06K 9/40* (2013.01); *G06K 9/46* (2013.01); *G06K 9/6267* (2013.01); *G06T 5/20* (2013.01); *G06T 7/62* (2017.01); *G06K 9/3233* (2013.01); *G06T 2207/10081* (2013.01); *G06T 2207/30061* (2013.01)

(58) Field of Classification Search
None
See application file for complete search history.

(56) References Cited

U.S. PATENT DOCUMENTS

| | | | |
|---|---|---|---|
| 5,319,549 | A | 6/1994 | Katsuragawa et al. |
| 5,740,268 | A * | 4/1998 | Nishikawa ............. G06K 9/527 |
| | | | 382/130 |

(Continued)

FOREIGN PATENT DOCUMENTS

| | | |
|---|---|---|
| JP | 1994-339476 A | 12/1994 |
| JP | 2003-010171 A | 1/2003 |

(Continued)

*Primary Examiner* — Hadi Akhavannik
(74) *Attorney, Agent, or Firm* — Mintz Levin Cohn Ferris Glovsky and Popeo, P.C.; Kongsik Kim; Jonathon Western

(57) ABSTRACT

A method of quantifying a medical image is disclosed herein. The method of quantifying a medical image includes acquiring regions of interest based on a medical image; filtering the sizes of the acquired regions of interest using length scale analysis; classifying the regions of interest whose sizes have been filtered, according to the sizes of the regions of interest; and visualizing the regions of interest whose sizes have been filtered, so that the regions of interest whose sizes have been filtered are distinguished from each other in the medical image according to the sizes of the regions of interest.

9 Claims, 13 Drawing Sheets

(51) Int. Cl.
  *G06K 9/62* (2006.01)
  *G06T 5/20* (2006.01)
  *G06T 7/62* (2017.01)
  *G06K 9/32* (2006.01)

(56) References Cited

U.S. PATENT DOCUMENTS

| | | |
|---|---|---|
| 6,898,303 B2 | 5/2005 | Armato, III et al. |
| 7,283,652 B2 | 10/2007 | Mendonca et al. |
| 7,460,732 B2 * | 12/2008 | Recht ................ G06K 9/00127 382/181 |
| 2004/0093166 A1 * | 5/2004 | Kil .......................... G01N 1/06 702/19 |
| 2005/0207630 A1 * | 9/2005 | Chan ...................... A61B 6/466 382/131 |
| 2005/0259854 A1 * | 11/2005 | Arimura ............... G06T 7/0012 382/130 |
| 2007/0248254 A1 * | 10/2007 | Mysore Siddu ..... G06K 9/4638 382/131 |
| 2010/0195883 A1 * | 8/2010 | Patriarche ........... G06K 9/3233 382/131 |

FOREIGN PATENT DOCUMENTS

| | | |
|---|---|---|
| JP | 2003-070781 A | 3/2003 |
| JP | 2004-174254 A | 6/2004 |
| JP | 4469594 B2 | 5/2010 |
| JP | 4730758 B2 | 7/2011 |
| KR | 10-1144964 B1 | 5/2012 |

* cited by examiner

FIG. 13
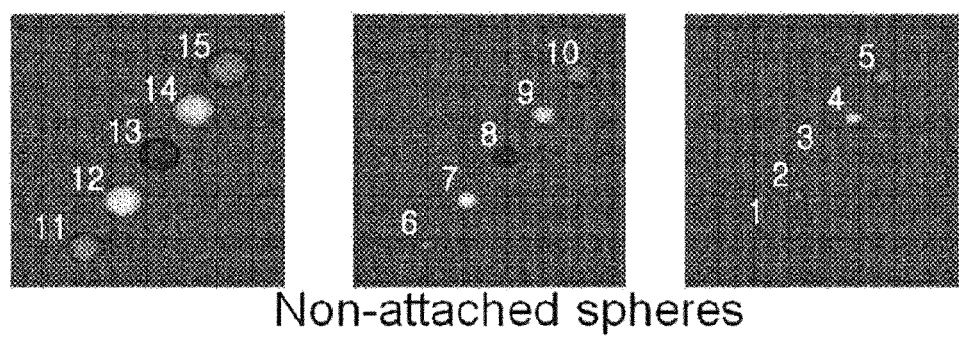
Non-attached spheres
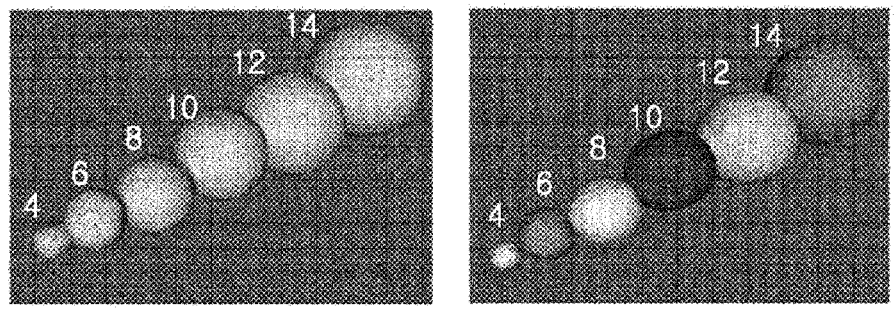
Attached spheres

# METHOD FOR QUANTIFYING MEDICAL IMAGE

CROSS-REFERENCE TO RELATED APPLICATION

This application is a continuation of PCT/KR2014/004974 filed on Jun. 4, 2014, which claims priority to Korean Patent Application No. 10-2013-0098549 filed on Aug. 20, 2013, which applications are incorporated herein by reference.

TECHNICAL FIELD

The present disclosure relates generally to a method of quantifying a medical image, and more particularly to a method of quantifying a medical image, which classifies regions of interest according to their size.

BACKGROUND ART

This section provides background information related to the present disclosure which is not necessarily prior art.

The lungs are organs that function to exchange $CO_2$ in blood with $O_2$ in air. It is important for the local alveoli of the lungs to be continuously supplied with new $O_2$ and blood. Various methods are used as methods of diagnosing a pulmonary disease, for example, a chronic obstructive pulmonary disease (COPD), such as emphysema or chronic bronchitis.

As an example of such a method, diffusing capacity of the lungs for carbon monoxide (DLco) is a medical test that measures the difference between the partial pressures of carbon monoxide in inspiration and expiration states. However, DLco provides only the average information of pulmonary functions, and neither distinguishes the left and right lungs from each other nor provides information based on the locations of the lungs.

Meanwhile, high-resolution computed tomography (CT) is widely used as a noninvasive means for estimating a change in a pulmonary structure attributable to CODP. For example, as shown in FIG. 1, a lung image is acquired using CT, and an index, such as the percentage of a low attenuation area (LAA %) in the lung image or an emphysema index (ED, related to the loss of pulmonary functions is employed.

Such CT-based LAA % or EI distinctively shows the left and right lungs, and shows the distribution of emphysema at a pixel level. However, only an emphysema image and an EI are not sufficient to provide objective information about the extent and local distribution of emphysema. For example, from a left emphysema image 1a of FIG. 1 and a right emphysema image 1b of FIG. 1, it can be seen that there is a similarity in the EI and that there is a significant difference in the size and distribution of emphysema. Although a doctor may visually and intuitively determine the size and distribution of the emphysema, a problem arises in that the determination is not objective.

Furthermore, since emphysema is indicative of the structural loss of the lungs, the anatomy of the lungs has a correlation with the size and distribution of emphysema. However, a problem arises in that the intuitive interpretation of a lung image or an EI, i.e., an average numerical value, cannot provide sufficient information about the correlation between the size and local distribution of emphysema and the anatomy of the lungs.

The paper "Longitudinal Study of Spatially Heterogeneous Emphysema Progression in Current Smokers with Chronic Obstructive Pulmonary Disease" by Naoya Tanabe, Shigeo Muro, Susumu Sato, Shiro Tanaka, Tsuyoshi Oguma, Hirofumi Kiyokawa, Tamaki Takahashi, Daisuke Kinose, Yuma Hoshino, Takeshi Kubo, Toyohiro Hirail, and Michiaki Mishima discloses a method of measuring LAA % and a yearly change in the type and number of emphysema clusters is disclosed. However, this paper does not disclose a method of classifying emphysema clusters or emphysemas themselves constituting the emphysema clusters according to their size.

SUMMARY OF THE DISCLOSURE

This section provides a general summary of the disclosure and is not a comprehensive disclosure of its full scope or all of its features.

According to one aspect of the present disclosure, there is provided a method of quantifying a medical image, including acquiring regions of interest based on a medical image; filtering the sizes of the acquired regions of interest using length scale analysis, and classifying the regions of interest, whose sizes have been filtered, according to the sizes of the regions of interest; and visualizing the regions of interest, whose sizes have been filtered, so that the regions of interest whose sizes have been filtered are distinguished from each other in the medical image according to the sizes of the regions of interest.

BRIEF DESCRIPTION OF THE DRAWINGS

The above and other objects, features and advantages of the present invention will be more clearly understood from the following detailed description taken in conjunction with the accompanying drawings, in which:

FIG. 13 is a diagram illustrating a phantom study in which emphysemas are modeled by spheres.

DETAILED DESCRIPTION OF THE DISCLOSURE

The present disclosure will now be described in detail with reference to the accompanying drawings.

Figure 1:
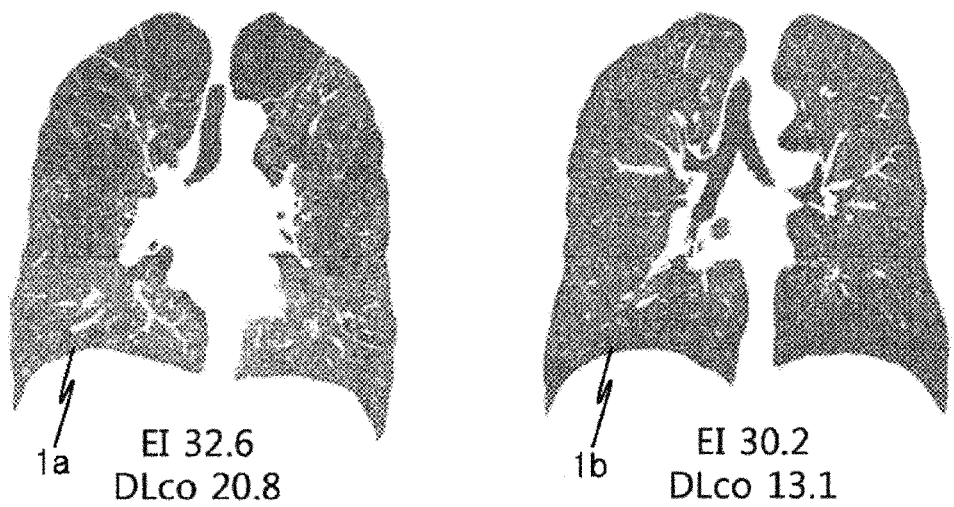
FIG. 1 is a diagram illustrating an example of an emphysema image acquired by thresholding a lung image.
Figure 2:
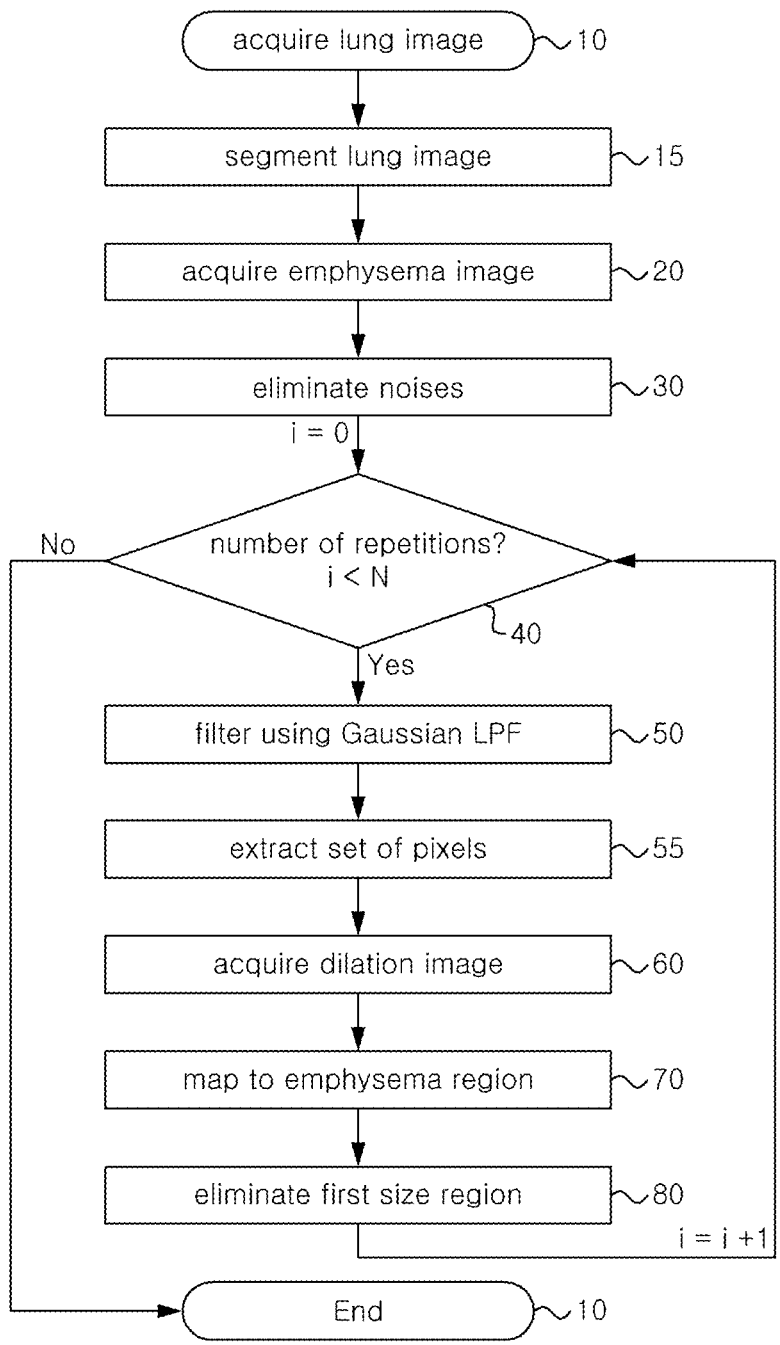
FIG. 2 is a diagram illustrating an example of a method of quantifying a medical image according to the present disclosure.

FIG. 2 is a diagram illustrating an example of a method of quantifying a medical image according to the present disclosure.

In the method of quantifying a medical image, first, regions of interest are generated at steps 10, 15 and 20 based on a medical image. Thereafter, the regions of interest are classified according to the sizes of the regions of interest at steps 40 to 80.

For example, the medical image is acquired by a medical imaging apparatus, and the regions of interest are extracted by thresholding the medical image.

Thereafter, noises are eliminated from the regions of interest, and the regions of interest are image-processed. The image processing is performed such that the intensity of each of the regions of interest is image-processed to have a correlation with the size of the corresponding region of interest. Thereafter, the size ranges of the regions of interest are determined based on the intensities of the image-processed regions of interest.

For example, the sizes of the regions of interest are filtered using length scale analysis. As a result, a region of interest (a first size region) having a first size range is acquired from the regions of interest. Thereafter, the first size region is eliminated from the regions of interest. The sizes of the regions of interest from which the first size region has been eliminated are filtered using length scale analysis. As a result, a region of interest (a second size region) having a second size range is acquired from the regions of interest.

Thereafter, the first size region and the second size region may be visualized such that they can be distinguished from each other in the medical image.

A method of quantifying a medical image will now be described in detail with reference to the accompanying drawings.

Figure 3:
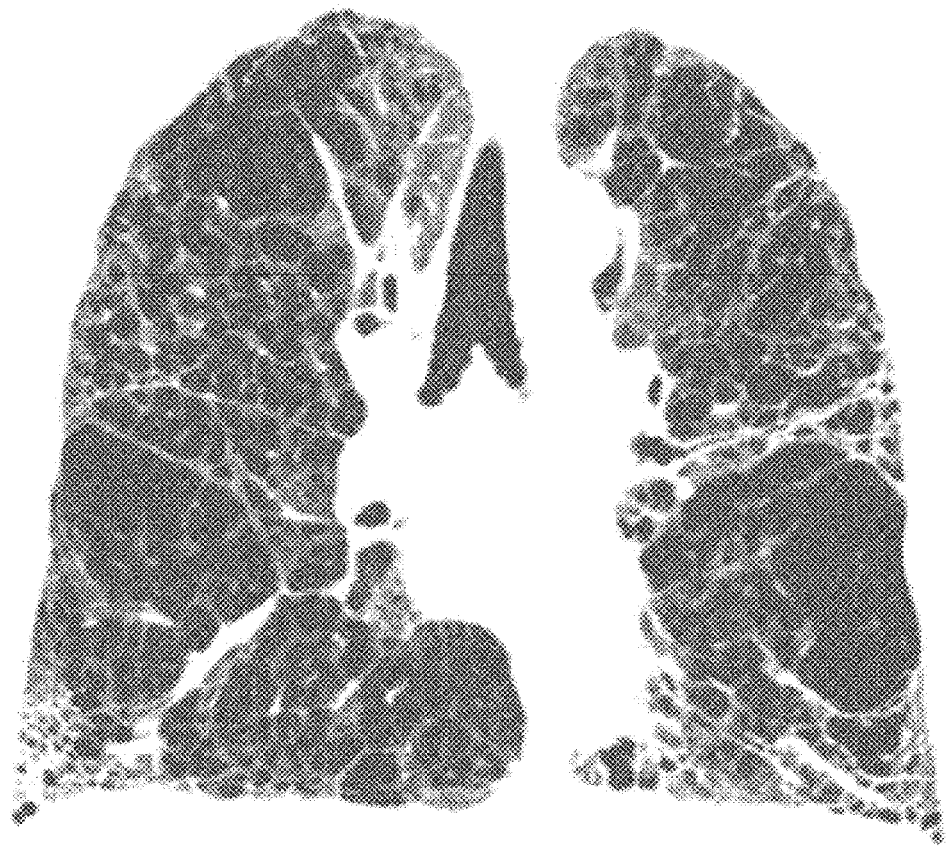
FIG. 3 is a diagram illustrating an example of an emphysema image acquired by thresholding a lung image.

FIG. 3 is a diagram illustrating an example of an emphysema image acquired by thresholding a lung image.

In the method of quantifying a medical image, first, a medical image is acquired by a medical imaging apparatus (at steps 10 and 15 of FIG. 2).

For example, an image of an organ is acquired by a medical imaging apparatus, such as a computed tomography (CT) scanner, a magnetic resonance imaging (MRI) scanner, or the like. Thereafter, regions of interest are extracted by thresholding the medical image (at step 20 of FIG. 2).

FIG. 3 illustrates an emphysema image generated by thresholding a lung image acquired by volumetric chest CT. A lung image shows the anatomy of the lungs and the ventilation of air. The air shown in the lung image includes not only air present in the normal airways of the lungs, but also air filling a region in which a structure (for example, an alveolus) of the lungs has been damaged.

For example, in a CT image, brightness is proportional to attenuation. Accordingly, air is shown as a low attenuation area (LAA). When a lung image is filtered at a threshold value of −950 HU, emphysema regions (regions of interest) exclusive of normal airways are extracted, and thus an emphysema image is acquired.

A uniform intensity may be assigned to the regions of interest for the purpose of the performance of the following process. For example, a maximum density value (MDV) of 225 may be assigned to the regions of interest.

Figure 4:
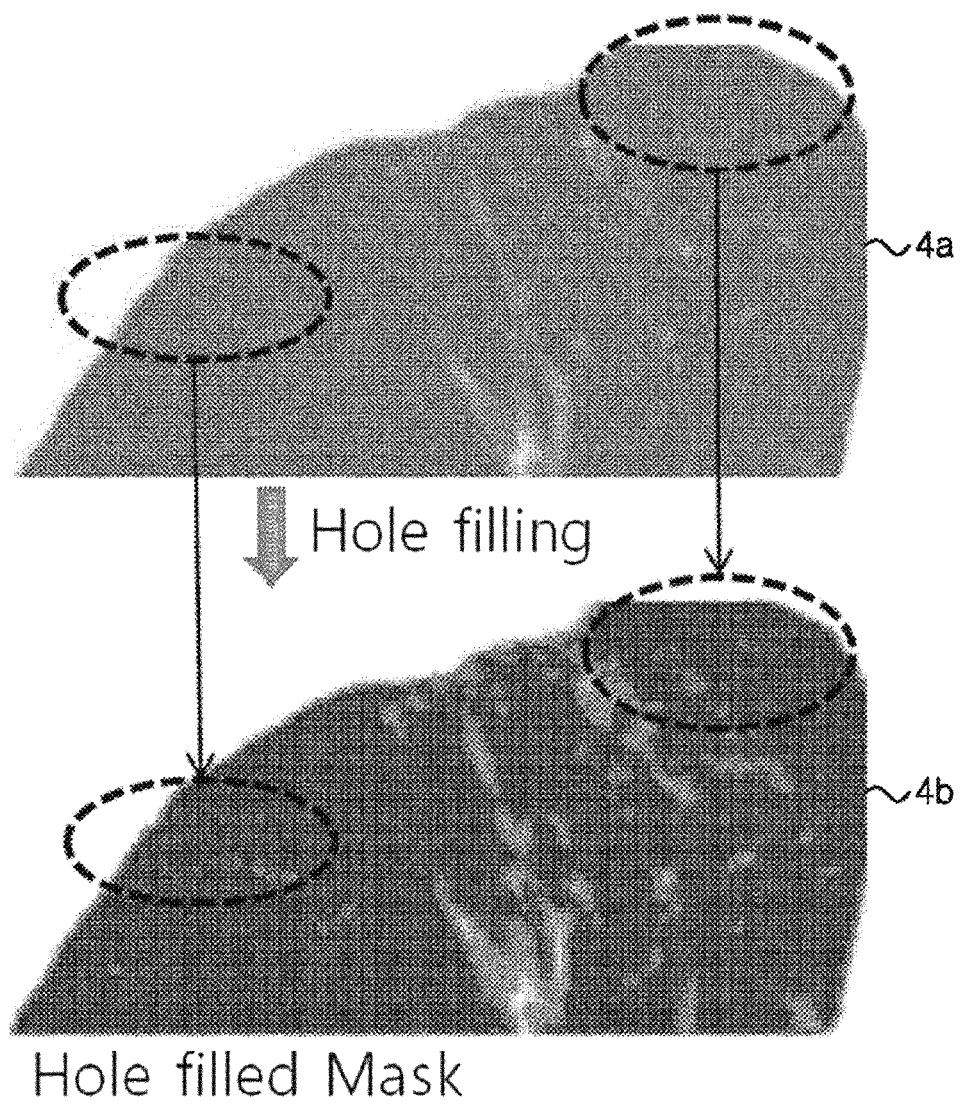
FIG. 4 is a diagram illustrating an example of a method of eliminating noises from an emphysema image.

FIG. 4 is a diagram illustrating an example of a method of eliminating noises from an emphysema image.

Small holes that appear in regions of interest before hole-filling 4a and that are determined to be noises are filled (at step 30 of FIG. 2) in regions of interest after hole-filling 4b. Holes appear in regions of interest due to the partial volume effect or noises. Although these holes have a size of about one or two pixels, the accuracy of the size filtering of the regions of interest is considerably degraded in the following process, and thus the holes are eliminated from the regions of interest. For example, the holes are filled using an appropriate filling filter.

Figure 5:
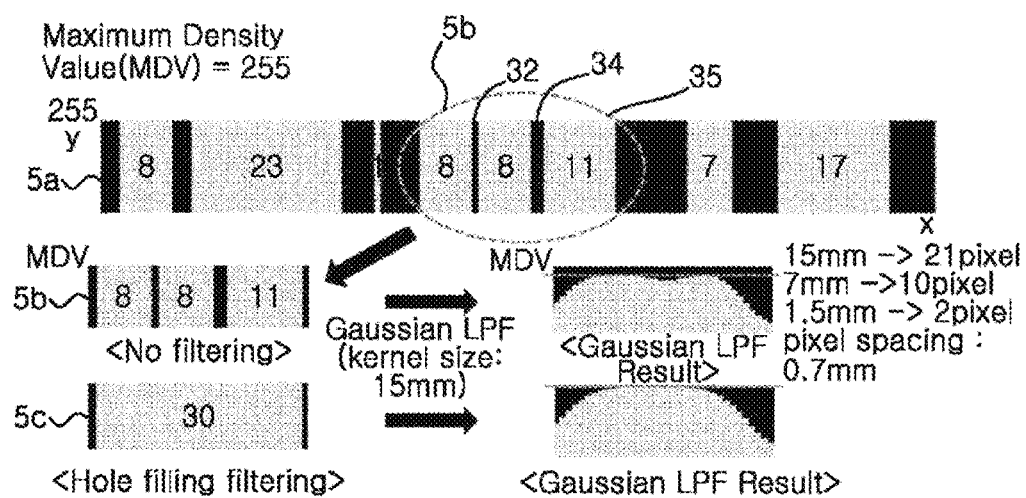
FIG. 5 is a diagram illustrating an example of a hole filling effect.

FIG. 5 is a diagram illustrating an example of a hole filling effect.

A region-of-interest image is acquired as three-dimensional (3D) volume data. Regions with emphysema and regions without emphysema are acquired from the region-of-interest image in a specific direction in the form of spectra, as shown in first spectrum 5a in FIG. 5. In first spectrum 5a of FIG. 5, hole-shaped noises 32 and 34 are illustrated.

If the hole-shaped noises are not eliminated, error may occur when the regions of interest are filtered according to a kernel size using a Gaussian LPF.

For example, referring to LPF result diagram of a second spectrum 5b of FIG. 5, when holes are not eliminated, the MDV of a region of interest 35 blurred by a Gaussian LPF is lower than a reference value. Accordingly, the region of interest substantially has a size of 30 but does not pass through the filter, and thus a great error occurs. In the present example, such noises are eliminated in advance. When holes are eliminated, as a third spectrum 5c of FIG. 5, the LPF result diagram of the second spectrum 5b has a region passing through the Gaussian LPF.

The following process of quantifying the regions of interest is performed using the regions of interest from which the noises have been eliminated as described above.

Figure 6:
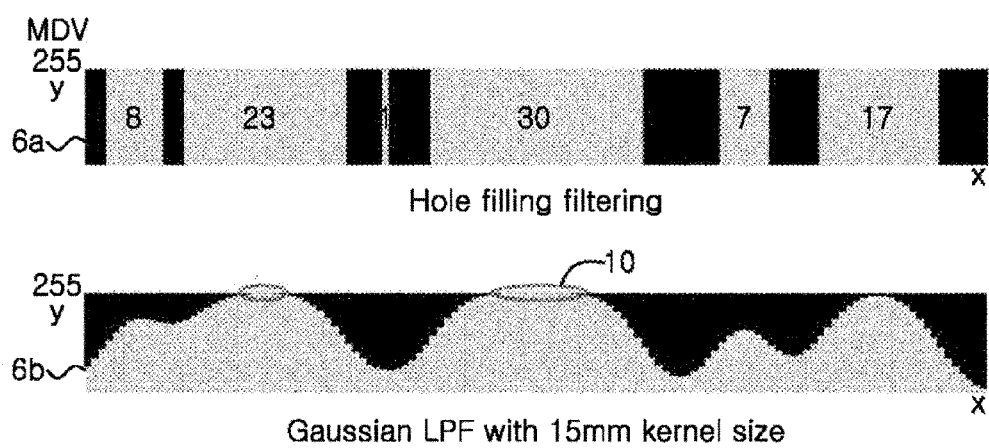
FIG. 6 is a diagram illustrating an example of a process of filtering regions of interest using a Gaussian low-pass filter (LPF)
Figure 7:
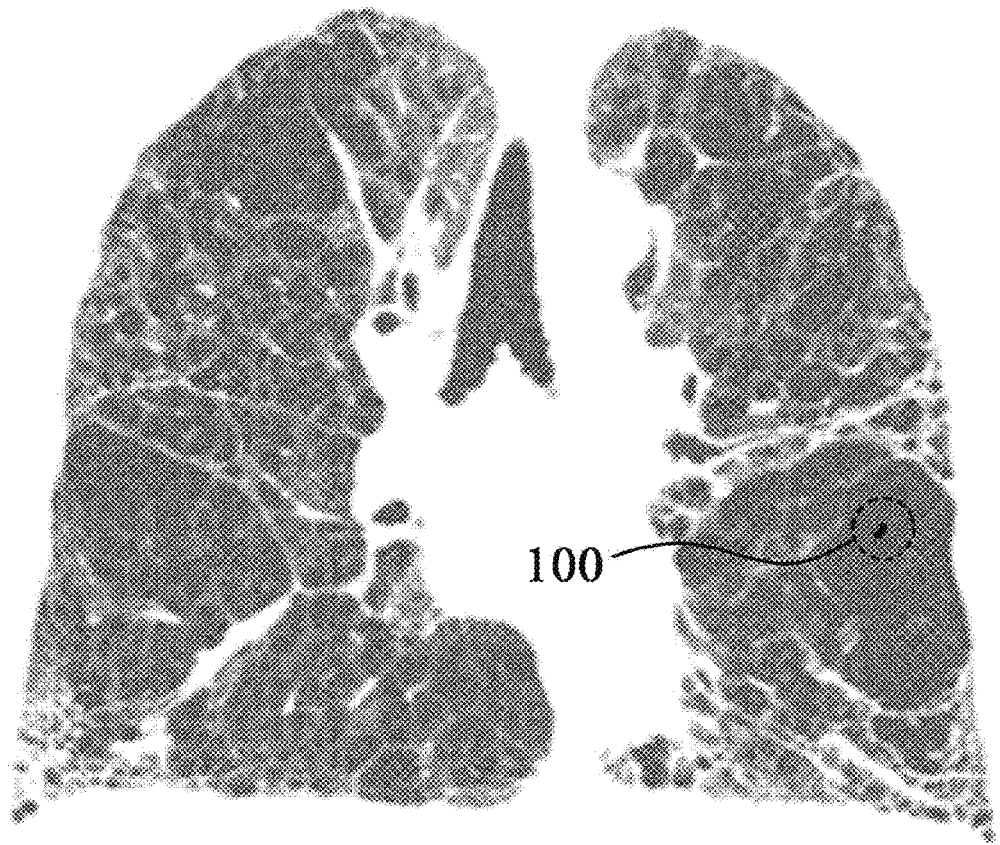
FIG. 7 is a diagram illustrating an example of extracting a set of pixels by filtering regions of interest using a Gaussian LPF.

FIG. 6 is a diagram illustrating an example of a process of filtering regions of interest using a Gaussian LPF. FIG. 7 is a diagram illustrating an example of extracting a set of pixels by filtering regions of interest using a Gaussian LPF.

Thereafter, the region-of-interest image from which noises have been eliminated is image-processed. The image processing is performed such that the intensity of each of the regions of interest is image-processed to have a correlation with the size of the corresponding region of interest. Thereafter, the size ranges of the regions of interest are determined based on the intensities of the image-processed regions of interest.

For example, length scale analysis may be used as a method of performing image processing and size filtering. In the present example, a method of performing size filtering using a Gaussian LPF is used as an example of the length scale analysis (at step 50 of FIG. 2).

First, when a Gaussian LPF is applied to the fourth region-of-interest spectrum 6a of FIG. 6, as a first kernel size condition, regions of interest are blurred, as shown in LPF result diagram 6b of FIG. 6. That is, the regions of interest are image-processed, and thus the edges thereof are processed to be smooth. When the filtering condition is set to a value equal to or larger than a first kernel size (for example, 15 mm), the regions of interest equal to or larger than 15 mm have a set of pixels 100 whose intensity corresponds to the MDV, as shown in LPF result diagram 6b of FIG. 6 (at step 55 of FIG. 2). As described above, the size range of a region of interest in which pixels whose intensity is equal to or higher than the MDV remain is determined to be the first size region.

The set of pixels 100 is shown in a region-of-interest image, as shown in FIG. 7.

Figure 8:
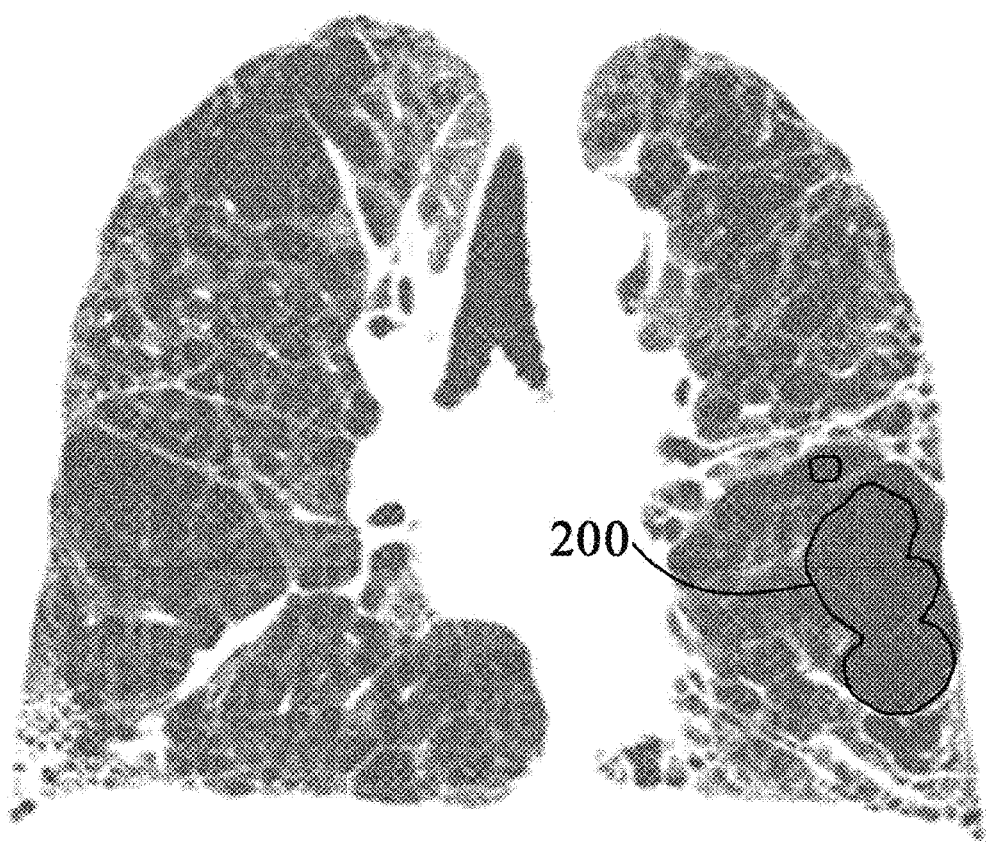
FIG. 8 is a diagram illustrating an example of generating a dilated region based on a set of pixels having passed through a Gaussian LPF.

FIG. 8 is a diagram illustrating an example of a process of generating a dilated region based on a set of pixels having passed through a Gaussian LPF.

Thereafter, a region of interest including the set of pixels 100 is restored based on the set of pixels. A dilation method may be used for image restoration, and the extent to which dilation is performed by the dilation technique is limited by the kernel size of the Gaussian LPF (at step 70 of FIG. 2).

The kernel size of the Gaussian LPF is set by taking into account the interval between the pixels. Since the set of pixels is a set of pixels having passed through the Gaussian LPF, the total width of pixels arranged along a rectilinear line in the set of pixels is equal to or smaller than the kernel size of the Gaussian LPF. Furthermore, the extent to which the dilated region is dilated is determined by the kernel size.

Figure 9:
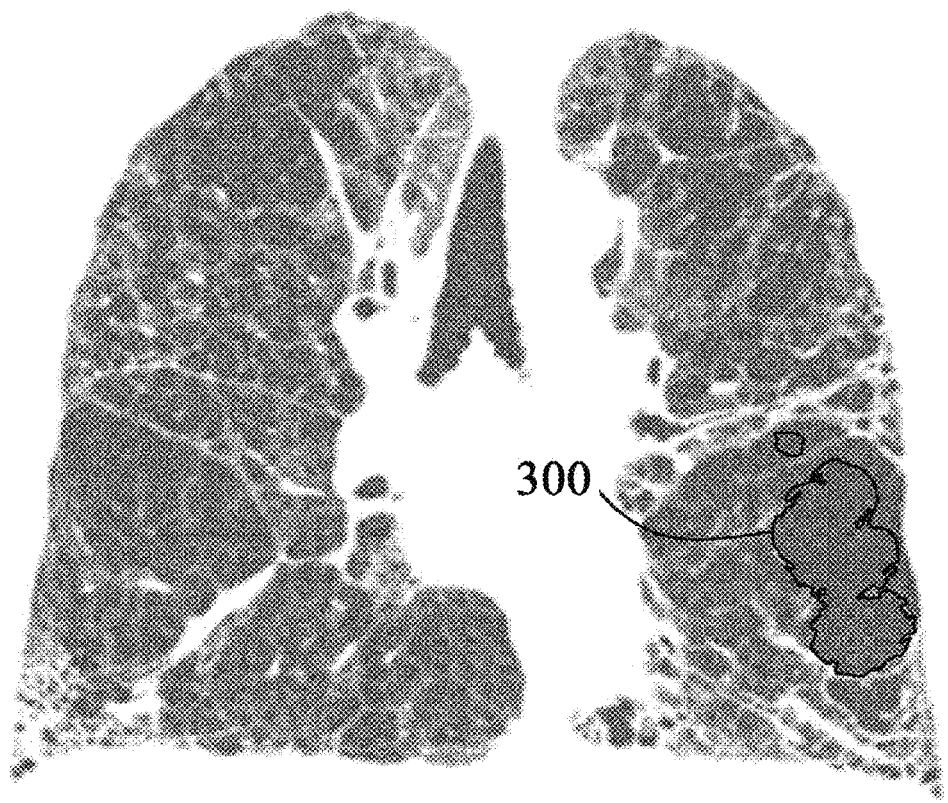
FIG. 9 is a diagram illustrating an example of generating a first size region based on a dilated region.
Figure 10:
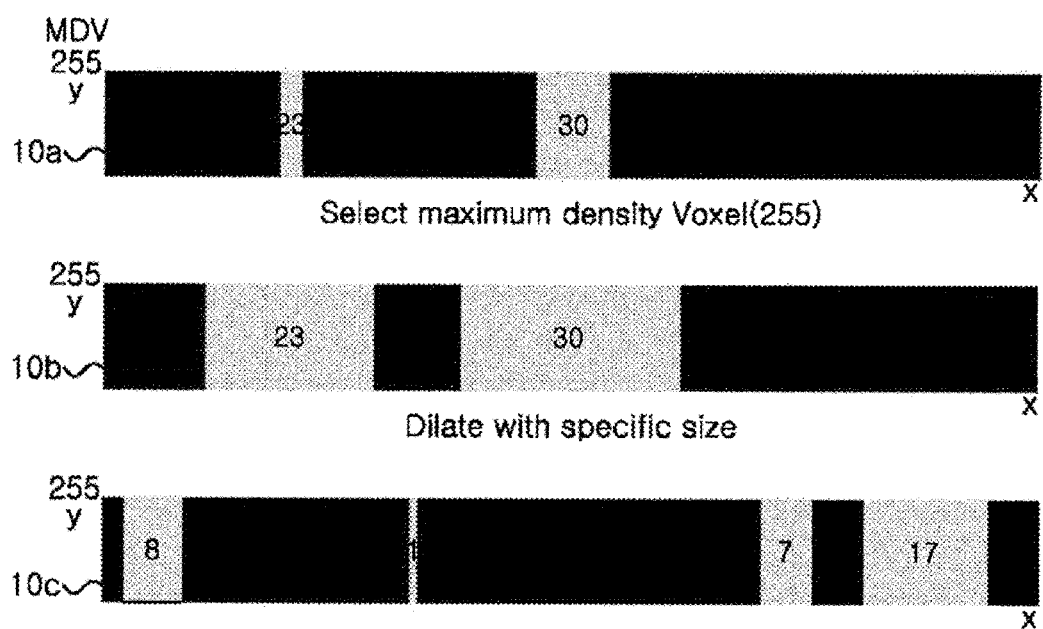
FIG. 10 is a diagram illustrating the processes of FIG. 7 through FIG. 9 using a spectrum image of regions of interest.

FIG. 9 is a diagram illustrating an example of a process of generating a first size region from a dilated region. FIG. 10 is a diagram illustrating the processes of FIG. 7 through FIG. 9 using a spectrum image of regions of interest.

A dilated region 200 (refer to spectrum 10b of FIG. 10) has been merely extended from the set of pixels 100 (refer to spectrum 10a of FIG. 10) in order to meet the kernel size, and has a contour that is different from that of an original region of interest. Accordingly, in order to restore the contour of the region of interest, the shape of the region of interest is restored by mapping the dilated region 200 to the region of interest including the set of pixels (at step 80 of FIG. 2).

The region of interest which has passed through the Gaussian LPF having the first kernel size condition and the shape of which has been restored, as described above, is defined as a first size region 300 (refer to spectrum 10c of FIG. 10).

Figure 11:
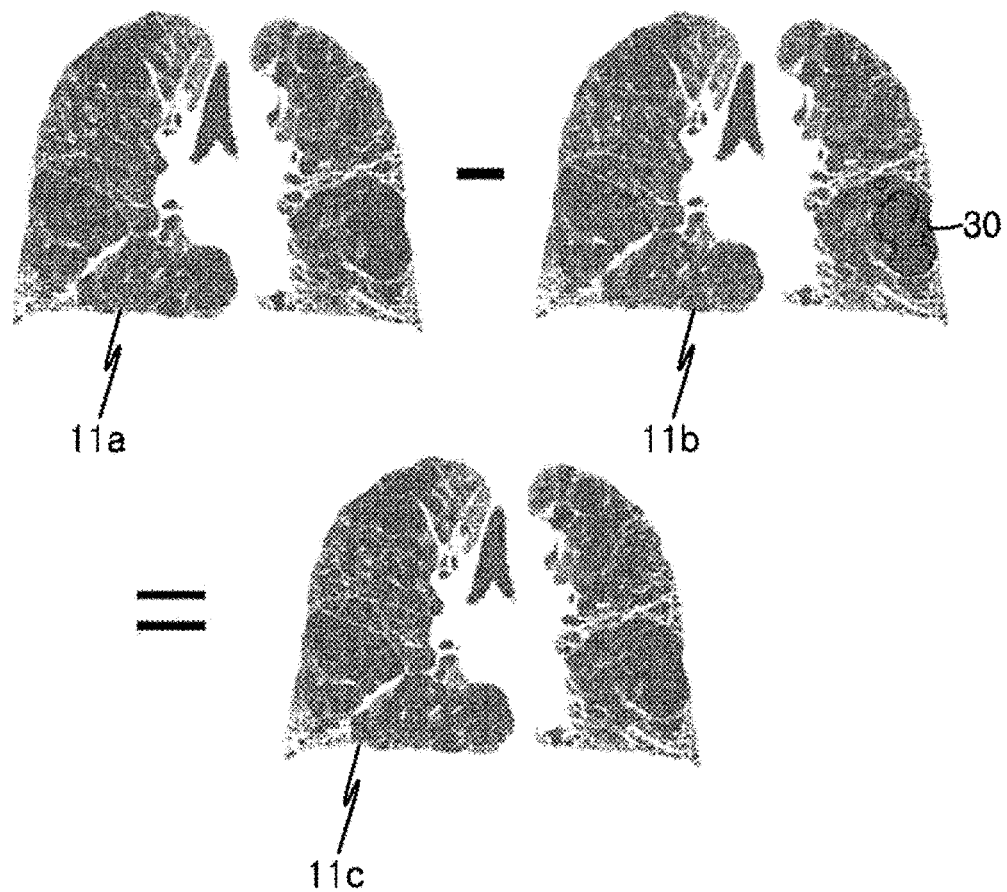
FIG. 11 is a diagram illustrating an example of eliminating a first size region from a region-of-interest image.

FIG. 11 is a diagram illustrating an example of a process of eliminating a first size region from a region-of-interest image.

The first size region 300 (see 11b of FIG. 11) is eliminated from a region-of-interest image (see 11a of FIG. 11) acquired by thresholding a lung image. As a result, a region-of-interest image from which the first size region 300 has been eliminated is acquired (see 11c of FIG. 11).

Figure 12:
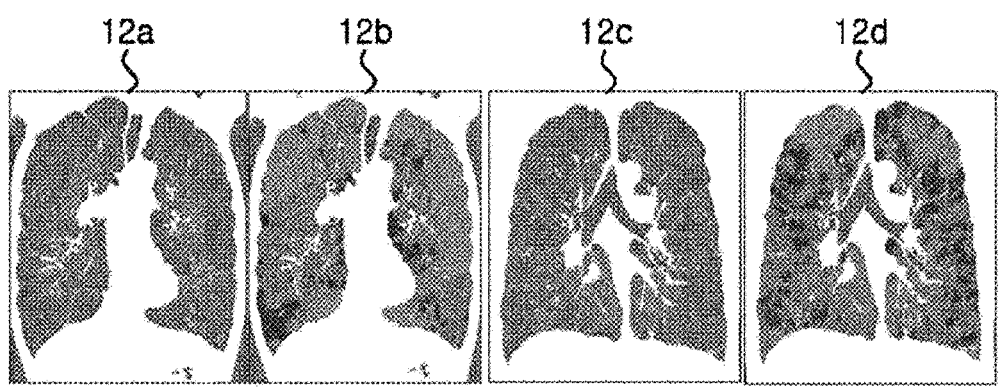
FIG. 12 is a diagram illustrating examples of regions of interest that are classified according to their size region by repeating size-based classification.

FIG. 12 is a diagram illustrating an example of regions of interest that are classified according to their size region by repeating size-based classification.

Thereafter, for example, after hole filling, the number of repetitions of the extraction of the size region is determined compared by N (at step 40 of FIG. 2). For example, in the determination of the number of repetitions, when i=0, kernel size k=15 is applied, when i=1, kernel size k=7 is applied, when i=2, kernel size k=1.5 is applied, and when i>3, a circulation process may be determined to be the termination of a loop.

For example, a second size region is extracted from a region-of-interest image from which a first size region has been eliminated. The second size region is eliminated from the image from which the first size region has been eliminated. A third size region is extracted from an image from which the second size region has been eliminated. The third size region is eliminated from the image from which the second size region has been eliminated. A fourth size region is extracted from an image from which the third size region has been eliminated. The first size region, the second size region, the third size region, and the fourth size region extracted as described above may be visualized, as shown in FIG. 12.

In FIG. 12, area distributions can be seen from two region-of-interest images (refer to 12a and 12c of FIG. 12), and there is no significant difference in the EI, i.e., the area ratio. However, it can be seen that although the size distributions of regions of interest are visually known, two processed images (refer to 12b and 12d of FIG. 12) in which regions of interest have been classified according to their size respectively, as in the present example, are required to quantify and objectively estimate the size distributions.

From 12b of FIG. 12, it can be seen that the number of first size regions volume2 is larger and the first size regions are distributed up to the lower regions of the lungs. From 12d of FIG. 12, it can be seen that the number of first size regions is small but a larger number of second size regions volumes3 are distributed. The present disclosure may additionally represent such size distributions in the form of values.

Referring to 12a and 12c of FIG. 12, it can be seen that for two patients, EIs are similar to each other, the size distributions of emphysemas are locally different from each other, and the types of sizes are different from each other, referring to 12b and 12d. From this, it can be seen that the extents of progression of emphysemas are different from each other.

FIG. 13 is a diagram illustrating a phantom study in which emphysemas are modeled by spheres.

The emphysemas were modeled by spheres having various sizes ranging from 1 mm to 15 mm. Sigma values derived from a Gaussian kernel were used. The accuracy or validity of examples of a method of quantifying a medical image may be estimated based on the results of the phantom study.

When the emphysemas are not close to each other (in the upper side of FIG. 13), the sizes of the emphysemas are accurately filtered in the size filtering of the emphysemas using a Gaussian LPF. However, when the emphysemas are in contact with each other (in the lower side of FIG. 13), the sizes of the emphysemas modeled by the spheres are underestimated.

Table 1 below shows the results of the actual tests of the method of quantifying a medical image according to the present example. The tests were conducted on 20 COPD patients having no local lesion, such as pneumonia, tuberculosis or the like, and were verified by expert thoracic radiologists with 7 years of experience. The patients included 19 males and 1 female, and the average age of the patients was 62.2.

TABLE 1

| Size | <1.5 mm | <7 mm | <15 mm | 15 mm< |
|---|---|---|---|---|
| Size-based EI (%) | 3.48 ± 1.97 | 12.85 ± 7.07 | 7.07 ± 7.88 | 4.11 ± 8.22 |
| r-value* (p-value**) | 0.499 | 0.726 | 0.769 | 0.940 |
| Incorrect estimation (%) | 0.00 ± 0.00 | 0.67 ± 0.20 | 0.50 ± 0.41 | 1.17 ± 0.26 |

In Table 1 above, the r-values* represent the Pearson correlation r values between the results of the blind visual evaluations of emphysemas by expert thoracic radiologists and the results of the method of quantifying a medical image according to the present example. The incorrect estimation % represents underestimation probability or overestimation probability.

Referring to Table 1 above, it can be seen that the method of quantifying a medical image described in the present disclosure is substantially valid because error is extremely small.

Various embodiments of the present disclosure will now be described.

(1) The method of quantifying a medical image, wherein the classifying the regions of interest may include: image-processing the regions of interest, wherein the regions of interest are image-processed such that the intensities of the image-processed regions of interest have correlations with the sizes of the image-processed regions of interest; and determining the size ranges of the regions of interest based on the intensities of the image-processed regions of interest.

(2) The method of quantifying a medical image, wherein the classifying the regions of interest may include: acquiring a first size region from the regions of interest by filtering the sizes of the regions of interest using length scale analysis; eliminating the first size region from the regions of interest; and acquiring a second size region by filtering the regions of interest, from which the first size region has been eliminated, using length scale analysis on a size basis.

(3) The method of quantifying a medical image, further including visualizing the first size region and the second size region so that they are distinguished from each other in the medical image.

(4) The method of quantifying a medical image, wherein the generating regions of interest may include: acquiring the medical image using a medical imaging apparatus; and extracting the regions of interest by thresholding the medical image.

(5) The method of quantifying a medical image, further including, before the classifying the regions of interest, eliminating noises by filling holes that appear in the regions of interest.

(6) The method of quantifying a medical image, wherein the generating regions of interest may include: acquiring an image of an organ using CT; and determining regions of lesion, extracted by thresholding the image of the organ, to be the regions of interest.

(7) The method of quantifying a medical image, wherein the acquiring a first size region may include: blurring the regions of interest using a Gaussian LPF; extracting a set of pixels, whose intensity is equal to or higher than a reference value, from the blurred regions of interest; generating a dilated region from the set of pixels using a dilation method; and generating the first size region by mapping the dilated region to a region of interest including the set of pixels.

(8) The method of quantifying a medical image, wherein the total width of pixels arranged along a rectilinear line within the set of pixels may be equal to or smaller than the kernel size of the Gaussian LPF, and the extent of dilation of the dilated region may be determined by the kernel size.

(9) The method of quantifying a medical image, wherein the generating regions of interest may include: acquiring a lung image using a medical imaging apparatus; and determining regions of lesion, extracted by thresholding the lung image, to be the regions of interest; and the classifying the regions of interest may include: blurring the regions of lesion using a Gaussian LPF having a first kernel size, and extracting a set of first pixels whose intensity is equal to or higher than a reference value; acquiring a first size region, belonging to a first size range, by means of a restoration process using the set of first pixels;

(10) eliminating the first size region from the regions of lesion; blurring the regions of lesion, from which the first size region has been eliminated, using a Gaussian LPF having a second kernel size, and extracting a set of second pixels whose intensity is equal to or higher than a reference value; and acquiring a second size region, belonging to a second size range, by means of a restoration process using the set of second pixels.

(11) A computer-readable storage medium having stored thereon a program for executing any one of the above methods on a computer.

The method of quantifying a medical image according to the present disclosure can accumulate data obtained by quantifying regions of interest in a medical image, thereby improving the accuracy and effect of diagnosis and treatment.

Furthermore, the method of quantifying a medical image according to the present disclosure can predict the diagnosis of a specific patient or the tendency of changes in emphysema based on the correlations between quantified data and the anatomy of the lungs.

Furthermore, the method of quantifying a medical image according to the present disclosure can determine the effect of reaction to a specific treatment through the quantitative comparison and evaluation of regions of interest, thereby being very useful to the development of a new treatment or medicine.

What is claimed is:

1. A method of quantifying a medical image, comprising:
    acquiring, by a processor in a computing system, regions of interest based on a medical image;
    filtering, by the processor, sizes of the acquired regions of interest using length scale analysis;
    classifying, by the processor, the regions of interest whose sizes have been filtered, according to the sizes of the regions of interest; and
    visualizing, by the processor, the regions of interest whose sizes have been filtered, so that the regions of interest whose sizes have been filtered are distinguished from each other in the medical image according to the sizes of the regions of interest,
    wherein the classifying comprises:
        acquiring a first size region from the regions of interest by filtering the sizes of the regions of interest using length scale analysis;
        eliminating the first size region from the regions of interest; and
        acquiring a second size region by filtering the regions of interest, from which the first size region has been eliminated, using length scale analysis on a size basis, and
    wherein the acquiring of the first size region comprises:
        blurring the regions of interest using a Gaussian LPF;
        extracting a set of pixels, whose intensity is equal to or higher than a reference value, based on the blurred regions of interest;
        generating a dilated region based on the set of pixels using a dilation method; and
        generating the first size region by mapping the dilated region to a region of interest including the set of pixels.

2. The method of claim 1, wherein the classifying comprises:
    image-processing the regions of interest to have intensities have correlations with sizes; and determining size ranges of the regions of interest based on the intensities of the image-processed regions of interest.

3. The method of claim 2, wherein:
the image-processing comprises blurring the regions of interest using a Gaussian low-pass filter (LPF); and
the determining comprises extracting a set of first pixels whose intensity is equal to or higher than a reference value after the regions of interest blurred by a Gaussian LPF having a first kernel size.

4. The method of claim 3, wherein the classifying comprises, before the blurring, assigning uniform intensity to the regions of interest.

5. The method of claim 1, further comprising, before the classifying, eliminating noises from the regions of interest by applying hole-filling into the regions of interest.

6. The method of claim 1, wherein the acquiring comprises:
acquiring an image of an organ using computed tomography (CT); and
determining the regions of interest based on regions of lesion extracted by thresholding the image of the organ.

7. The method of claim 1, wherein a total width of pixels arranged along a rectilinear line within the set of pixels is equal to or smaller than a kernel size of the Gaussian LPF, and an extent of dilation of the dilated region is determined by the kernel size.

8. A metod of qualifying a medical image, comprising:
acquiring, by a processor in a computing system, regions of interest based on a medical image;
filtering, by the processor, sizes of the acquired regions of interest using length scale analysis;
classifying, by the processor, the regions of interest whose sizes have been filtered, according to the sizes of the regions of interest; and
visualizing, by the processor, the regions of interest whose sizes have been filtered, so that the regions of interest whose sizes have been filtered are distinguished from each other in the medical image according to the sizes of the regions of interest, wherein:
the acquiring comprises:
acquiring the medical image using a medical imaging apparatus; and
determining the regions of interest based on regions of lesion extracted by thresholding the medical image; and
the classifying comprises:
blurring the regions of lesion using a Gaussian LPF having a first kernel size;
extracting a set of first pixels whose intensity is equal to or higher than a first reference value;
acquiring a first size region having a first size range, by means of a restoration process using the set of first pixels;
eliminating the first size region from the regions of lesion;
blurring the regions of lesion, from which the first size region has been eliminated, using a Gaussian LPF having a second kernel size;
extracting a set of second pixels whose intensity is equal to or higher than a second reference value; and
acquiring a second size region having a second size range, by means of a restoration process using the set of second pixels.

9. A non-transitory computer-readable medium containing program instructions executed by a processor installed in a computing system providing a medical image, wherein the program instructions comprise:
program instructions that acquire regions of interest based on a medical image;
program instructions that filter sizes of the acquired regions of interest using length scale analysis;
program instructions that classify the regions of interest whose sizes have been filtered, according to the sizes of the regions of interest; and
program instructions that visualize the regions of interest whose sizes have been filtered, so that the regions of interest whose sizes have been filtered are distinguished from each other in the medical image according to the sizes of the regions of interest,
wherein the program instructions that classify the regions of interest whose sizes have been filtered comprises:
program instructions that acquire a first size region from the regions of interest by filtering the sizes of the regions of interest using length scale analysis;
program instructions that eliminate the first size region by filtering the regions of interest; and
program instructions that acquire a second size region by filtering the regions of interest, from which first size region has been eliminated, using length scale analysis on a size basis, and
wherein the program instructions that acquire the first region comprises:
program instructions that blur the regions of interest using a Gaussian LPF;
program instructions that extract a set of pixels, whose intensity is equal to or higher than a reference value, based on the blurred regions of interest;
program instructions that generate a dilated region based on the set of pixels using a dilation method; and
program instructions that generate the first size region by mapping the dilated region to a region of interest including the set of pixels.

* * * * *